(12) United States Patent
Mustapha et al.

(10) Patent No.: US 9,790,688 B2
(45) Date of Patent: Oct. 17, 2017

(54) APPARATUS, SYSTEM AND METHOD FOR DETECTING DEFECTS IN BUILDING STRUCTURES

(75) Inventors: Gamal K. Mustapha, Surrey (CA); Jason G. Teetaert, Vancouver (CA); Gregory P. Jaman, Langley (CA); Alistair C. Burrows, Steinbach (CA); Ryan Ramchandar, Winnipeg (CA); Stephen Liao, Winnipeg (CA); Geoffrey Chen, Pinawa (CA); Chris Buzunis, Headingly (CA)

(73) Assignee: SMT Research Ltd., Vancouver (CA)

( * ) Notice: Subject to any disclaimer, the term of this patent is extended or adjusted under 35 U.S.C. 154(b) by 1023 days.

(21) Appl. No.: 12/716,461

(22) Filed: Mar. 3, 2010

(65) Prior Publication Data

US 2010/0225341 A1 Sep. 9, 2010

Related U.S. Application Data

(60) Provisional application No. 61/158,598, filed on Mar. 9, 2009.

(51) Int. Cl.
*E04D 13/00* (2006.01)
*G01N 27/20* (2006.01)
*G01N 27/02* (2006.01)

(52) U.S. Cl.
CPC ........... *E04D 13/006* (2013.01); *G01N 27/02* (2013.01); *G01N 27/20* (2013.01); *G01N 27/205* (2013.01)

(58) Field of Classification Search
CPC ...... G01N 27/20; G01N 27/205; G01N 27/02; E04D 13/006
(Continued)

(56) References Cited

U.S. PATENT DOCUMENTS 3,967,197 A 6/1976 Anderson
4,543,525 A 9/1985 Boryta et al.
(Continued)

FOREIGN PATENT DOCUMENTS

CA 1168707 6/1984
CA 2618092 C 4/2004
(Continued)

OTHER PUBLICATIONS

D. Derome et al.; "Methods for the Assessment of Moisture Content of Envelope Assemblies"; Proceedings for Performance of Exterior Envelopes of Whole Buildings VIII: Integration of Building Envelopes; pp. 1-13; Clearwater Beach, Florida, United States; Dec. 2-7, 2001.
(Continued)

*Primary Examiner* — Patrick Assouad
*Assistant Examiner* — Christopher McAndrew
(74) *Attorney, Agent, or Firm* — Nexus Law Group LLP; Nicholas P. Toth (57) ABSTRACT

An apparatus, system and method for detecting defects in building structures is provided. The apparatus includes a detector operable to determine an indication of the defect; and a transmitter operable to wirelessly transmit the indication from the apparatus to a central controller. The system includes the detection unit; a locator operable to determine the location of the detection unit; and a memory for storing the indication and the location in association with each other. The memory may be part of a central controller in wireless communication with the detection unit. The apparatus or central controller may include a processor operable to determine from a plurality of measurements performed by the detection unit a resultant measurement vector indicating a direction from the detection unit toward the defect. The detection unit may be operable to autonomously change its
(Continued)

location. A display showing resultant measurement vectors at various locations can be produced.

26 Claims, 4 Drawing Sheets

(58) Field of Classification Search
USPC .................................................. 324/457, 718
See application file for complete search history.

(56) References Cited

U.S. PATENT DOCUMENTS

| | | | |
|---|---|---|---|
| 4,565,965 A | | 1/1986 | Geesen |
| 5,081,422 A | | 1/1992 | Shih |
| 5,721,489 A | * | 2/1998 | Weaver et al. ............... 324/329 |
| 5,850,144 A | | 12/1998 | Howells et al. |
| 6,175,310 B1 | | 1/2001 | Gott |
| 6,331,778 B1 | * | 12/2001 | Daily ...................... G01M 3/16 324/512 |
| 6,377,181 B1 | | 4/2002 | Kroll et al. |
| 6,581,045 B1 | * | 6/2003 | Watson ......................... 705/400 |
| 7,126,486 B2 | | 10/2006 | Kroll et al. |
| 7,142,123 B1 | | 11/2006 | Kates |
| 7,292,155 B2 | | 11/2007 | Vokey et al. |
| 7,449,892 B2 | * | 11/2008 | Wiswell et al. ............... 324/457 |
| 7,554,345 B2 | * | 6/2009 | Vokey ........................... 324/718 |
| 7,652,481 B2 | * | 1/2010 | Vokey ........................... 324/523 |
| 7,872,479 B2 | * | 1/2011 | Lorenz et al. ................ 324/691 |
| 2005/0057258 A1 | * | 3/2005 | Colahan ............... G01N 27/205 324/501 |
| 2006/0092031 A1 | | 5/2006 | Vokey et al. |
| 2006/0235611 A1 | * | 10/2006 | Deaton et al. ................ 701/207 |
| 2007/0279067 A1 | * | 12/2007 | Wiswell ................. G01R 29/12 324/457 |
| 2008/0143349 A1 | * | 6/2008 | Lorenz .................... G01M 3/16 324/691 |
| 2009/0044595 A1 | * | 2/2009 | Vokey ................... E04D 13/006 73/1.17 |

FOREIGN PATENT DOCUMENTS

| | | |
|---|---|---|
| CA | 2510354 A1 | 9/2005 |
| CA | 2520202 C | 11/2006 |
| CA | 2606466 A1 | 11/2006 |
| CA | 2596212 A1 | 1/2008 |
| CA | 2599087 C | 2/2008 |
| CA | 2613308 C | 3/2008 |
| CA | 2618999 C | 4/2008 |
| CA | 2513387 C | 6/2008 |
| CA | 2583006 C | 10/2008 |
| DE | 3701130 A1 | 7/1988 |
| DE | 102005046025 A1 | 3/2007 |
| GB | 2393517 A | 3/2004 |
| WO | 99/31632 A1 | 6/1999 |
| WO | 02/21114 A1 | 3/2002 |
| WO | 2004/008133 A1 | 1/2004 |
| WO | 2005/010837 A2 | 2/2005 |
| WO | 2005/098403 A1 | 10/2005 |
| WO | 2006/014111 A2 | 2/2006 |
| WO | 2007/037830 A1 | 4/2007 |

OTHER PUBLICATIONS

G. Jaman & S. Hussain; "Structural Monitoring using Wireless Sensors and Controller Area Network"; Proceedings of the Fifth Annual Conference on Communication Networks and Services Research; pp. 26-34; Fredericton, New Brunswick, Canada; May 11-14, 2007.
D. M. Bailey et al.; "Survey of Passive Leak Detection Technologies for Membrane Roofing"; USACERL Technical Report FM-94/04; US Army Corps of Engineers; Mar. 1994.
G. Chen et al.; "Autonomous Electric Field Vector Mapping for Leak Detection on Building Roofs"; (B.Sc. Computer Engineering at University of Manitoba Faculty of Engineering 2009); [unpublished].
Detec Systems; "4 Ways Detec Systems Keeps Active Watch Over Your Roof"; online: <http://www.detecsystems.com/downloads/DSCS04-RoofMonitoring4web.pdf>; (accessed Jun. 16, 2009).
Detec Systems; "Leak Detection Methods for Roof Assemblies"; online: <http://www.detecsystems.com/roof_membrane_scanning.php>; (accessed Jun. 16, 2009).
C. Eichhorn; "Electric Field Vector Mapping"; International Leak Detection Ltd; Jun. 2002.
C. Eichhorn & C. Miller; "A New Leak Detection Technique"; New York Real Estate Journal; Jan. 2002.
Elektro Geesen Messgerate GmbH; "Leak Detector HG4"; online: <http://www.geesen.de/allgem2.htm>; (accessed Jun. 17, 2009).
Elektro Geesen Messgerate GmbH; "Flatroof—Leak Detector HG4 Operating Instructions"; online: <http://www.geesen.de/userbook.htm>; (accessed Jun. 17, 2009).
F. Granne; "Methods for quality assurance of low-sloped roofs"; Building Physics 2002—6th Nordic Symposium; 2002.
W. Healy; "Moisture Sensor Technology—A Summary of Techniques for Measuring Moisture Levels in Building Envelopes"; American Society of Heating, Refrigerating and Air-Conditioning Engineers (ASHRAE) Transactions: Research; pp. 232-242; 2003.
H. Kunzel; "Moisture Risk Assessment of Roof Constructions by Computer Simulation in comparison to the Standard Glaser-Method"; International Building Physics Conference, Eindhoven; Sep. 2000.
Progreo Monitoring; "ProGeo Monitoring of North America"; online: <http://www.progeomonitoring.com/?pg=smartex_lp_function>; (accessed Jun. 16, 2009).
Progeo Monitoring; "Smartex Roof Leak Detection by Progeo Monitoring of North America"; online: <http://www.reedconstructiondata.com/companies/products/smartex-roof-leak-protection-systems-by-progreo-monitoring-north/>; (accessed Jun. 16, 2009).
K. Roberts; "The Electrical Earth Leakage Technique for Locating Holes in Roof Membranes"; Proceedings of the Fourth International Symposium on Roofing Technology; pp. 347-351; Sep. 1997.
W. Rossiter, Jr.; [untitled]; Fourth International Symposium on Roofing Technology; Sep. 1997.
M. Said; "Measurement Methods of Moisture in Building Envelopes—A Literature Review"; International Journal of Architectural Heritage; v. 1, No. 3; pp. 293-310; Jul. 2007.
SMT Research Ltd.; "Wireless Precision Data Acquisition Node"; RS-1056 Rev. 2 Data Sheet; Winnipeg, Manitoba, Canada; Oct. 2007.
S. Wood; "Non-Invasive Roof Leak Detection Using Infrared Thermography"; InfraMation 2004 Proceedings; Jul. 2004.

* cited by examiner

APPARATUS, SYSTEM AND METHOD FOR DETECTING DEFECTS IN BUILDING STRUCTURES

CROSS-REFERENCE TO RELATED APPLICATIONS

This application claims priority of provisional application 61/158,598, filed Mar. 9, 2009, the entire contents of which are hereby incorporated by reference.

BACKGROUND OF THE INVENTION

1. Field of Invention

This invention relates to civionics and, in particular, to an apparatus, system and method for detecting defects in building structures.

2. Description of Related Art

Detecting and locating defects such as leaks in building structures, including detecting and locating leaks in low-slope roofs of buildings, can assist in the development, repair, maintenance and appraisal of such building structures. With the introduction of green roofs, leaks are even more detrimental and difficult to locate as water is intentionally held on the roof within landscaping materials.

Leaks in building structures may be detected by visual inspection; however, leaks are not always visible or may not become visible until after such leaks have caused damage to the structure. Also, visible effects of a leak may be located distally from the leak, thereby failing to accurately indicate the location of the detected leak. The accuracy of leak detection by visual inspection depends on the skill and experience of the person conducting the visual inspection. Visual inspection alone does not provide a transmittable record of the location nor size of a visually detected leak.

Leaks in a low-sloped roof of a building may be detected by flood testing in which a large body of water is maintained on the roof for a long time period, such as several days, while water level changes are monitored and visual inspections for leaked water are periodically performed. However, such periodic visual inspections alone do not provide a transmittable record of the location nor size of a visually detected leak.

Leaks in a low-sloped roof may be detected by use of a negative pressure container placed in contact with a liquid distributed over a section of the roof, such that visible bubbles are created where leaks exist. However, the mere appearance of visible bubbles do not provide a transmittable record of the location nor size of the detected leak.

Leaks in a low-sloped roof can be detected by injecting smoke into a positive pressure region created beneath the roof and visually inspecting the upper surface of the roof for escaping smoke. However, the mere appearance of escaping smoke does not provide a transmittable record of the location nor size of the detected leak.

An indication of the possibility of a leak in a building structure may be obtained by measuring the humidity of materials of the structure. However, an abnormal humidity level does not necessarily indicate the presence of a leak, as it may indicate the presence of a spill or other cause instead. Also, a leak in a structure often causes a section of the structural materials much larger than the size of the leak to have increased humidity, thereby failing to accurately locate the leak.

U.S. Pat. No. 4,565,965 issued Jan. 21, 1986 to Geesen discloses a method and apparatus for locating leaks in flat roofs, in which electrical pulses are transmitted along a moisture path through a leak and along the wetted flat roof to the roof edge. The wetted flat roof is scanned by sensors made of a pair of rods connected to a display scale indicating the magnitude of electrical current through the rods. The magnitude becomes greater as the leak location is approached.

Training and experience are required by a skilled technician in order to detect and locate a leak using the method and apparatus of Geesen. Accordingly, the accuracy and completeness in detecting and locating leaks is dependent on the skills, training and experience of the technician using the method and apparatus of Geesen. The method and apparatus of Geesen does not facilitate the analysis of multiple measurements; does not provide a transmittable record of the location nor value of a measurement being taken; and does not provide a transmittable record of the location nor size of any detected leaks.

U.S. Pat. No. 4,543,525 issued on Sep. 24, 1985 to Boryta et al. discloses a method for determining a leak in a flat roof. A grounding electrode is attached to the reinforcing steel rods in concrete supporting the roof, roof drains are plugged, and the roof is flooded with an electrically conductive fluid such as salt water to a depth of several inches. An electrical potential is established between the fluid and the support structure. Boryta et al. also disclose a leak detector for determining a leak in a pond liner of electrically insulating material. The leak detector has a pair of spaced apart probes electrically connected to each other through a galvanometer for measuring electrical current through the probes. Detecting and locating a leak requires multiple successive measurements. The leak detector may be handheld, or in the form of a tripod supported by wheels and provided with undisclosed means for pulling or pushing the detector across the pond.

Training and experience are required by a skilled technician in order to detect and locate a leak using the method and leak detector of Boryta et al. Accordingly, the accuracy and completeness in detecting and locating leaks is dependent on the skills, training and experience of the technician using the method and leak detector of Boryta et al. The leak detector of Boryta et al. does not facilitate the analysis of multiple measurements; does not provide a transmittable record of the location nor value of a measurement being taken; and does not provide a transmittable record of the location nor size of any detected leaks.

Canadian patent No. 2,613,308 to Vokey discloses a method and apparatus for locating a leak in a membrane on top of a horizontal roof deck. The leak is located by sweeping over the upper surface of the membrane with a manually operable carriage. A measuring and switching circuit generates a voltage having a positive attached to the roof deck and a negative attached to conductive brushes on the carriage. The conductive brushes include an outer set of conductive brushes for detecting the leak at distance from the leak and an inner conductive brush for detecting the leak when the carriage is directly over the leak.

Training and experience are required by a skilled technician in order to detect and locate a leak using the method and apparatus of Vokey. Accordingly, the accuracy and completeness in detecting and locating leaks is dependent on the skills, training and experience of the technician using the method and apparatus of Vokey. The apparatus of Vokey does not facilitate the analysis of multiple measurements; does not provide a transmittable record of the location nor value of a measurement being taken; and does not provide a transmittable record of the location nor size of any detected leaks.

United Kingdom patent application publication No. 2,393,517 to Neil Graham Ferguson Adams discloses an instrument for locating defects in non-conductive materials. The instrument includes a handheld, mobile component connected to a stationary component by a multi-conductor lead. The handheld component includes a central probe surrounded by four outer probes, all of which are fixed to a non-conductive supporting plate. The probes may be telescopic and spring-loaded. On top of the plate are situated eight lines of light emitting diodes (LEDs), each line being at 45° to the previous. The stationary component includes a pulsing power supply connected between earth, or ground, of the non-conductive material and the central probe of the handheld component. The potential difference between each pair of diametrically opposite probes is found and, depending on their relative magnitude, a net vector representing the direction of current flow is calculated. This is quantized to the nearest 45° and the line of LEDs corresponding to this angle illuminated.

However, the instrument as described by Adams is limited in resolution to eight lines of LEDs; does not facilitate the analysis of multiple measurements taken in sequence; does not provide a transmittable record of the location nor value of a measurement being taken; and does not provide a transmittable record of the location nor size of any detected leaks.

An object of the invention is to address the above shortcomings.

SUMMARY

The above shortcomings may be addressed by providing, in accordance with one aspect of the invention, an apparatus for detecting a defect in a building structure. The apparatus includes: (a) a detector operable to determine an indication of the defect; and (b) a transmitter operable to wirelessly transmit the indication from the apparatus to a central controller.

The apparatus may include a locator operable to determine the location of the detection unit, and wherein the transmitter is operable to wirelessly transmit to the central controller the location in association with the indication. The locator may include at least one of an automated vision system, a global positioning system, a local beacon positioning system, an odometer, an optical sensor and an accelerometer. The apparatus may include a probe terminating in a pair of spaced-apart terminals dimensioned for immersing into a fluid situated adjacent a first side of an electrically insulating member of the building structure, the electrically insulating member being supported at a second side thereof by an electrically conductive member of the building structure, the apparatus being operable to produce a measurement of electrical current flow within the fluid between the terminals when a potential difference is being generated between the electrically conductive member and the fluid. The apparatus may include a processor operable to determine from a plurality of the measurements a resultant measurement vector indicating a direction from the location toward the defect. The apparatus may include a display having a display screen, the apparatus being operable to display the resultant measurement vector on the display screen. The apparatus may include a substantially circular guard electrically connectable to the electrically conductive member, the guard terminating in one or more guard terminals dimensioned for immersing into the fluid. The apparatus may include a handle attachable to the detector. The apparatus may include at least one motor-driven wheel for moving the detector from the location to a second location. The apparatus may include a robotic controller for autonomously controlling the at least one motor-driven wheel.

In accordance with another aspect of the invention, there is provided a system for detecting a defect in a building structure. The system includes: (a) a detection unit operable to determine an indication of the defect; (b) a locator operable to determine the location of the detection unit; and (c) a memory for storing the indication and the location in association with each other.

The detection unit may include a device selected from the group consisting of: a negative pressure containment device, a smoke detection device, a humidity detection device and an electrical field detection device. The system may be operable to determine the direction from the location toward the defect. The detection unit may include a probe terminating in a pair of spaced-apart terminals dimensioned for immersing into a fluid situated adjacent a first side of an electrically insulating member of the building structure, the electrically insulating member being supported at a second side thereof by an electrically conductive member of the building structure, and wherein the detection unit is operable to produce a measurement of electrical current flow within the fluid between the terminals when a potential difference is being generated between the electrically conductive member and the fluid. At least one of the detection unit and the central controller may be operable to determine from a plurality of the measurements a resultant measurement vector indicating the direction from the location toward the defect. At least one of the detection unit and the central controller may be operable to display the resultant measurement vector on a pixel display. The system may include an electric grid adjacent the electrically insulating member at the first side, and an electrical source connectable between the electric grid and the electrically conductive member, the electrical source being operable to generate the potential difference. The system may be operable to adjust a measurement gain of the detection unit and adjust the potential difference. The detection unit may be operable to autonomously change its location. The locator may include at least one of an automated vision system, a global positioning system, a local beacon positioning system, an odometer, an optical sensor and an accelerometer. The detection unit may include a substantially circular guard electrically connectable to the electrically conductive member.

In accordance with another aspect of the invention, there is provided a method of detecting a defect in a building structure. The method involves: (a) determining by a detection unit an indication of the defect; (b) determining the location of the detection unit; and (c) storing in a memory the indication and the location in association with each other.

Determining by a detection unit an indication of the defect may involve determining the direction from the location toward the defect. Determining by a detection unit an indication of a defect may involve: (a) generating an electrical potential difference between an electrically conductive member of the building structure and a fluid situated adjacent a first side of an electrically insulating member of the building structure, the electrically insulating member being supported at a second side thereof by the electrically conductive member; and (b) producing a measurement of electrical current flow within the fluid between a pair of spaced-apart terminals of a probe of the detection unit. Determining by a detection unit an indication of the defect may involve determining from a plurality of the measurements a resultant measurement vector indicating the direction from the location toward the defect. The method may involve transmitting the indication to a central controller by wireless communications. The method may involve displaying the resultant measurement vector on a pixel display. The method may involve repeating steps (a), (b) and (c) above at a second location. Repeating steps (a), (b) and (c) above at a second location may involve moving autonomously from the location to the second location. Repeating steps (a), (b) and (c) above at a second location may involve repeating steps (a), (b) and (c) above at the second location closer to the defect than the location.

In accordance with another aspect of the invention, there is provided an apparatus for detecting a defect in a building structure. The apparatus includes: (a) a base having a first base side and a second base side opposite the first base side, the base having attached thereto at the first base side a plurality of probes terminating in a plurality of pairs of terminals, the terminals being arranged in a substantially circular pattern and projecting from the first base side in a first projection direction, each the terminal being dimensioned for immersing into a fluid situated adjacent a first side of an electrically insulating member of the building structure, the electrically insulating member being supported at a second side thereof by an electrically conductive member of the building structure, the apparatus being operable to produce a measurement of electrical current flow within the fluid between the terminals when a potential difference is being generated between the electrically conductive member and the fluid; and (b) a handle attachable to the base for projecting from the second side in a second projection direction substantially opposite the first projection direction, the handle being dimensioned to apply when attached substantially uniform pressure in the first projection direction to the terminals when pressure in a direction toward the base is applied to the handle.

The apparatus may include a substantially circular guard terminating in one or more guard terminals dimensioned for immersing into the fluid, the one or more guard terminals circumscribing the terminals, the guard being electrically connectable to the electrically conductive member.

Other aspects and features of the present invention will become apparent to those of ordinary skill in the art upon review of the following description of embodiments of the invention in conjunction with the accompanying figures and claims.

BRIEF DESCRIPTION OF THE DRAWINGS

In drawings which illustrate by way of example only embodiments of the invention.

DETAILED DESCRIPTION

Figure 1:
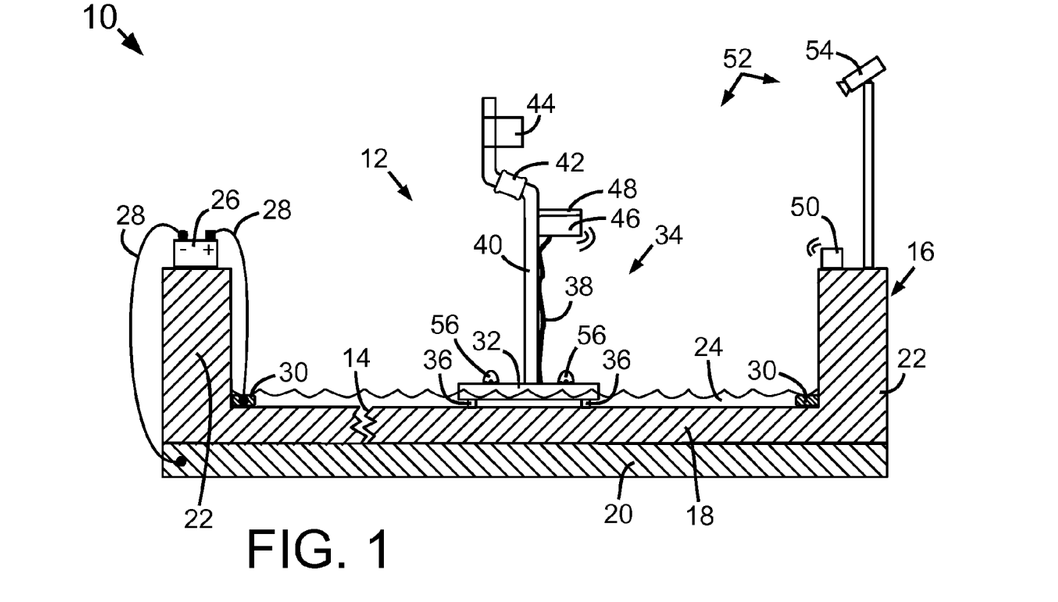
FIG. 1 is a side view of an apparatus according to a first embodiment of the invention.

Referring to FIG. 1, a system according to a first embodiment of the invention is shown generally at 10. The system 10 includes an apparatus 12, which is useable for detecting and locating a defect such as the leak 14 shown in the building structure 16.

In the exemplary illustration of FIG. 1, the structure 16 is a building rooftop made of an insulating layer 18 fixed to a support 20. In typical buildings, the insulating layer 18 is intended to be weather-resistant and is generally made of an electrically insulating material such as plastic, asphalt, ceramic, other suitable roofing materials, or any combination thereof. The insulating layer 18 may support aggregate, landscaping, green roofing or other materials, for example. The support 20 often includes or is made of structural materials such as steel, concrete, wood, or any combination thereof, and is generally electrically conductive.

FIG. 1 shows a single leak 14, however, any number of leaks 14 may exist in the building structure 16, including there being no leak 14 at all. Two spaced-apart and opposing walls 22 shown in FIG. 1 are not necessarily drawn to scale nor a necessary feature of the building structure 16. In general, various embodiments of the apparatus 12 are useful for locating defects in any kind of structure made of various materials and having any particular dimensions. The apparatus 12 in various embodiments may be or include a negative pressure container, a smoke detector, a humidity detector, an electrical field detector, other suitable device for detecting a defect or otherwise sensing an indication of a defect, or any combination thereof for example.

Where use is made of an electrical field detector, the insulating layer 18 is preferably wetted by fluid on top of the insulating layer 18, such as by the electrically conductive water 24 shown in FIG. 1. An electrical potential difference is created between the water 24 and the support 20, such as by an electrical generator 26 connected by generator connections 28 between the support 20 and an electrically conductive building guard 30 in contact with the water 24. Although FIG. 1 shows the electrical generator 26 as a direct current (DC) source, such as a battery, the electrical generator 26 may be any suitable device for generating direct current (DC), alternating current (AC), electrical pulses or other electrical waveforms, or any combination thereof. In at least some uses with at least some embodiments, the electrical generator 26 is a programmable generator which may be remotely controlled via wireless or wired connection. In various uses, any one or more of the electrical generator 26, the generator connections 28 and the building guard 30 may be temporarily installed or permanently fixed to the building structure 16. For clarity of illustration, the building guard 30, the insulating layer 18, including the walls 22, and the support 20 are shown in cross-section in FIG. 1. Typically, the building guard 30 is temporarily installed or permanently fixed as a circuit surrounding the area of the structure 16 to be tested for leaks 14. Where such test area is the entire surface of a rooftop, for example, the building guard 30 is preferably installed or fixed around the outer edges of the rooftop adjacent any walls 22 present as shown in FIG. 1. Although not shown in FIG. 1, the building guard 30 may include one or more electrically connected closed paths surrounding areas of the building structure 16 intended to be excluded from the electrical field detection. Such areas of non-interest may be drains or other known penetrations of the insulating layer 18 that need not be detected by use of the system 10, including for example defects such as the leak 14 after already being detected such as by use of the system 10.

Still referring to FIG. 1, the apparatus 12 in the first exemplary embodiment includes a base 32 having attached thereto a probe 34 for sensing electrical current flow within the electrically conductive water 24. The probe 34 of FIG.

1 includes a pair of spaced-apart probe terminations 36 projecting from the base 32. In the first embodiment, the probe terminations 36 are dimensioned for sensing electrical current flow within the water 24 between the probe terminations 36 when in contact with the water 24. The probe terminations 36 of the first embodiment form rigid projections as shown in FIG. 1, however, in variations the probe terminations 36 may form semi-rigid projections, flexible projections, resilient projections, bristles, tassels, molded protrusions, or any combination thereof. Additionally or alternatively, the probe terminations 36 may be telescopic and/or resiliently projecting from the base 32. The base 32 and probe terminations 36 may be variously dimensioned for suitable use on insulating layers 18 supporting different types of aggregate, landscaping or green roofing materials, for example.

Figure 2:
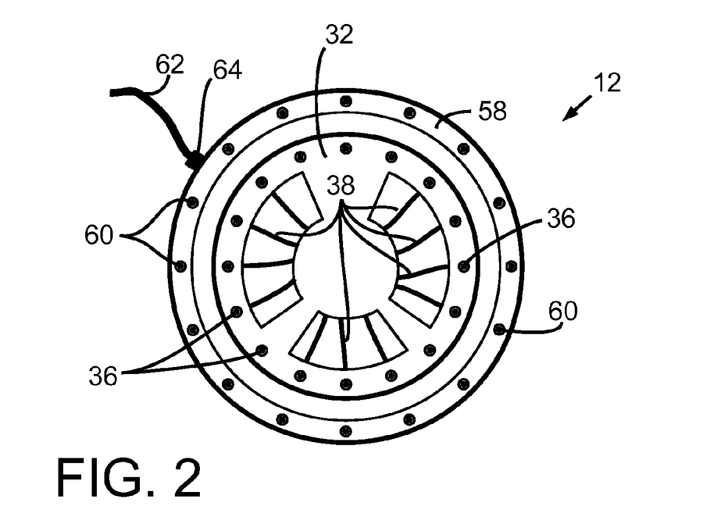
FIG. 2 is a bottom view of the apparatus shown in FIG. 1, showing probes attached to a base of the apparatus and a guard surrounding the base.

Referring to the bottom view of FIG. 2, the apparatus 12 in a variation includes eight (8) probes 34 attached to the base 32. The eight probes 34 terminate in sixteen (16) probe terminations 36 preferably arranged circularly such that the two probe terminations 36 of each probe 34 are diametrically opposite each other, although any suitable arrangement of spaced-apart probe terminations 36 is within the scope contemplated by the present invention.

Referring to FIGS. 1 and 2, various techniques known in the art for measuring electrical current flow between each pair of probe terminations 36 include measuring voltage across a resistive medium (not shown) through which the electrical current flows, sensing electromagnetic energy induced by the electrical current flow, etc., are within the scope contemplated by the present invention. In at least some embodiments, the system 10 is operable to take precise voltage differential measurements.

The probes 34 shown in FIGS. 1 and 2 include probe connections 38, which are electrically connected to the probe terminations 36 to advantageously permit electrical current measurements to be performed distally from the probe terminations 36.

Referring to FIG. 1, a handle 40 projects from an upper side of the base 32 opposite the side at which the terminations 36 attach to the base 32. The handle 40 of the first embodiment includes a hand grip 42 and an arm support 44, and is permanently attached to the base 32. In various embodiments (not shown in FIG. 1), the handle 40 may be removably attachable to the base 32, telescopic, folding, configurable for storage, or any combination thereof for example.

When configured for use as shown in FIG. 1, the handle 40 is advantageously dimensioned for facilitating the application of substantially uniform pressure among circularly arranged probe terminations 36 when pressure is applied to the handle 40 in a direction toward the base 32. For example, the handle 40 may be dimensioned and attached to the base 32 at a central or near central position of the base 32 such that the hand grip 42 is positioned for transmitting to the base 32 in a substantially uniform manner a generally downward force applied to the hand grip 42 by a user (not shown).

In the first embodiment shown in FIG. 1, the electrical measurement of current flow within the water 24 between any given pair of probe terminations 36 is performed by electronic circuitry such as a measurement device (not visible in FIG. 1) housed within a controller 46 attached to the handle 40. Preferably, such measurement device is connected to the probe terminations 36 via the probe connections 38. The controller includes in some embodiments a display unit 48 as shown in FIG. 1, for displaying measurement results and other user information. The display unit 48 may employ any suitable display technique, including being a liquid crystal display (LCD) or other display having pixel-based display screen, for example.

The system 10 in at least some embodiments is operable to determine the location of the apparatus 12. In such embodiments, the system 10 may include an automated vision system, a global positioning system, a local beacon positioning system, an odometer, an optical sensor, an accelerometer, other locating device or system, or any combination thereof for example.

In the exemplary system 10 shown in FIG. 1, the controller 46 is operable to communicate wirelessly with one or more beacons 50 having known positions so as to determine the position of the apparatus 12. Additionally or alternatively, the controller 46 is operable in at least some embodiments to determine the location of the apparatus 10 via satellite communications with one or more satellites (not shown) of a global positioning system.

Also shown in FIG. 1 is an optional automated vision system 52, which includes a camera 54 for obtaining images of the apparatus 10 and its surroundings. Automated processes of the system 10 are operable to analyze images obtained by the camera 54 to determine the location of the apparatus 12. Preferably, use of the automated vision system 52 involves a calibration process in which the apparatus 12 is positioned at various known positions (e.g., the corners of the outer boundary of a flat rooftop) and an image of the test area and the apparatus 12 is obtained by the camera 54. The system 10 thereafter is operable to determine subsequent positions of the apparatus 12 relative to the calibrated positions. In at least some embodiments, the apparatus 12 includes markers 56 to facilitate the automated vision processing of images obtained by the camera 54. For example, the markers 56 may be infra-red beacons or other sources of infra-red energy and the camera 54 may be an infra-red detection camera operable to detect images in the infra-red portion of the electromagnetic spectrum.

Referring to FIG. 2, a variation of the first embodiment includes a probe guard 58 generally circumscribing the base 32 of the apparatus 12. In further variations, the probe guard 58 may be permanently attached to the apparatus 12, removably attachable to the apparatus 12, non-fixedly mountable to the apparatus 12 when the apparatus 12 is generally in an upright position, or configurable by other suitable configuration.

FIG. 2 shows the bottom of the probe guard 58 having attached thereto guard terminations 60 similarly dimensioned to the probe terminations 36. However, in general the guard terminations 60 may have any suitable dimensions and rigidity and be made of any suitable material, including not being present at all, provided electrical contact with the water 24 can be made by the probe guard 58 when electrical contact with the water 24 is being made by the probe terminations 36. In at least some embodiments of the present invention, the probe guard 58 is height adjustable relative to the base 32 of the apparatus 12 such that the bottom of the probe guard 58 extends an adjustable distance relative to the bottom of the probe terminations 36. Additionally or alternatively, the guard terminations 60 may be telescopic and/or resiliently projecting from the probe guard 58.

In use, the probe guard 58 of the apparatus 12 in accordance with the first embodiment and variations thereof may be used in place of the building guard 30. In such use, the probe guard 58 is electrically connectable to the electrical generator 26, such as by the reference cable 62 shown in FIG. 2. In variations, the reference cable 62 at one end 64 thereof may be permanently attached or removably connectable to the probe guard 58, for example, and the reference cable 62 at its end opposite the end 64 may be permanently attached or removably connectable to the electrical generator 26 or similar, or any combination thereof. When the probe guard 58 is being used in place of the building guard 30, the effective test area can be made to be the area circumscribed by the probe guard 58 and electrical current flow within such test area can be measured between probe terminations 36, for example.

Additionally or alternatively, one or more guard terminations 60 and one or more probe terminations 36 may be switchably connected to one terminal of the electrical generator 26, with the other terminal of the electrical generator 26 being electrically connected to the support 20. Electrical current flow through the one or more guard terminations 60 indicates a defect outside the area circumscribed by the probe guard 58, while electrical current flow through the one or more probe terminations 36 indicates a defect located within the area circumscribed by the probe guard 58.

In at least some uses, the probe guard 58 of the apparatus 12 in accordance with the first embodiment and variations thereof may be used in conjunction with the building guard 30. In a first example of such use, the probe guard 58 may be electrically connected via the reference cable 62 to a voltmeter (not shown), which may be housed within the controller 46 for example. Such voltmeter is electrically connected between the probe guard 58 and the support 20 such that the system 10 is operable to determine the extent of any voltage loss between the building guard 30 and the probe guard 58. A notable voltage loss may indicate the need for further wetting of the insulating layer 18, the addition of an electrolyte such as salt, or other steps to improve the electrical conductivity of the water 24. The system 10 may, for example, generate an alarm or other user alert upon detection of a notable voltage loss. In embodiments having a probe guard 58 connected to a voltmeter for assessing the conductivity of the water 24, it is not necessary for the probe guard 58 to circumscribe the base 32 and such probe guard 58 may comprise as few as a single guard termination 60. In a second example of such use, the probe guard 58 may include probes 34 such that the system 10 is operable to selectably use probes 34 having pairs of probe terminations 36 spaced apart by different distances. In variations, the apparatus 12 may include further probes 34 (not shown) attached to the base 32 and having pairs of probe terminations 36 spaced apart by distances less than those of the probe terminations 36 shown in FIG. 2. In some embodiments, selectable probes 34 of different dimensions are selectable to advantageously facilitate detecting and locating leaks 14 of different dimensions and/or distances from a given location of the apparatus 12. Selectable probes 34 may be retractably selectable, selectable by switching electrical connections, or otherwise selectable, for example.

Figure 3:
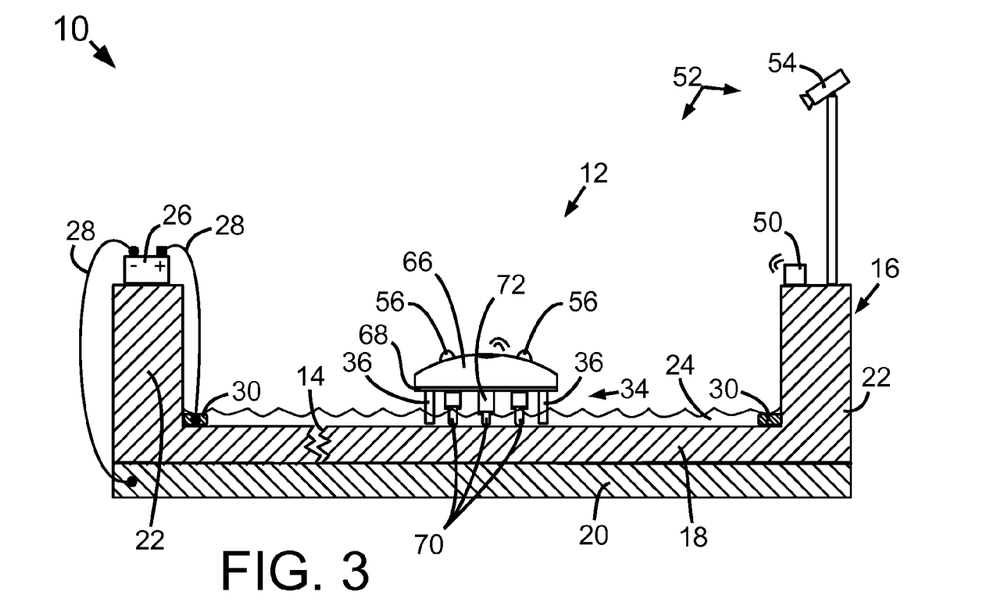
FIG. 3 is a side view of an apparatus according to a second embodiment of the invention.
Figure 4:
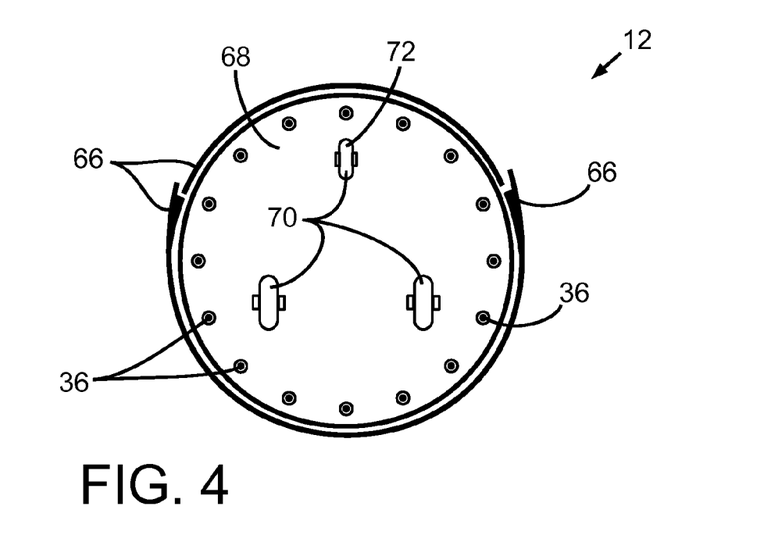
FIG. 4 is a bottom view of the apparatus shown in FIG. 3, showing an arrangement of wheels of the apparatus.

Referring to FIGS. 3 and 4, the system 10 in accordance with a second embodiment includes the apparatus 12 modified from that shown in FIGS. 1 and 2. The apparatus 12 of the second embodiment includes the controller 46 (not visible in FIGS. 3 and 4) enclosed within a housing 66, which is attached to a wheeled base 68. Also shown attached to the wheeled base 68 are three wheels 70, at least one of which is motor-driven. The motorized wheel 72 is driven by a motor (not visible in the Figures), which is typically enclosed within the housing 66.

In the second embodiment shown in FIGS. 3 and 4, the controller 46 is operable to control the motor or multiple motors (not visible in the Figures) to propel the apparatus 12, steer the apparatus 12, or both propel and steer the apparatus 12. Any suitable arrangement for changing the location of the apparatus 12 is within the scope contemplated by the present invention.

The apparatus 12 of the second embodiment includes at least one probe 34 and at least one probe termination 36, and may include eight (8) probes and sixteen (16) diametrically opposed probe terminations 36 as shown in the bottom view of FIG. 4. The dimensions and materials of the probe terminations 36 according to the second embodiment may be identical, similar, analogous or different from those of the probe terminations 36 of the first embodiment. For example, the probe terminations 36 of the second embodiment may be made of a semi-rigid or flexible material and dimensioned for dragging along the insulating layer 18 in contact with the water 24 while the apparatus 12 is being propelled and steered. In variations, one or more probe terminations 36 may be resiliently attached to corresponding probes 34 and/or the wheeled base 68, for example.

According to the second embodiment, the controller 46 is operable to control autonomous propulsion and steering of the apparatus 12 while performing electrical measurements using the probes 34. In this manner, the automated collection of measurement data advantageously facilitates extensive data collection. In variations, the apparatus 12 is operable to autonomously change its location while collecting measurement data in accordance with any suitable technique for detecting and/or locating a defect in the building structure 16, including negative pressure containment, smoke detection, humidity detection, electrical field detection, and any combination thereof for example. In such variations, the apparatus 12 is operable to autonomously change its location toward a direction selected randomly, including possibly changing its location to a randomly selected new location within a defined sub-area of the test area; toward a selected defined sub-area of the test area; along a predefined scanning path; away from or around an obstacle; toward the defect as determined in response to any previous measurement results; or any combination thereof, for example. The apparatus 12 is operable to change its location by a distance selected randomly, in accordance with measurement data, in accordance with user input, in accordance with parameters of the test area, or any combination thereof for example.

The apparatus 12 as shown in FIG. 3 includes two markers 56 for use by the automated vision system 52 of the system 10. Additionally or alternatively, the apparatus 12 as shown in FIG. 3 is operable to communicate wirelessly with the beacon 50 for determining the location of the apparatus 12 as it moves. As is the case with the first embodiment, the system 10 of the second embodiment may determine the location of the apparatus 12 in any suitable manner. According to the second embodiment, the system 10 is operable to determine the location of the apparatus 12 at which each measurement is performed.

The apparatus 12 of the second embodiment and variations thereof may include further features of an autonomous robot, including autonomous navigation, bump sensors, cliff sensors, wall sensors, collision avoidance behaviour, wheel drop sensors, differential drive system for moving in a straight line or in an arc in a forward or backward direction, wheel encoding, odometry, path tracking for full coverage of a test area, terrain sensors, uneven terrain navigation and suspension, similar or related features, or any combination thereof, for example. Additionally or alternatively, the apparatus 12 of the second embodiment may include features particular to detecting defects in building structures 14, including the housing 66 being waterproof or water-resistant, clearance dimensions such that the wheeled base 68 is adequately clear of the water 24 in typical circumstances, and other similar or related features or combination thereof for example. In the second embodiment shown in FIG. 3, the wheel clearance is preferably between 1 and 10 cm, and is typically between 2 and 4 cm where the apparatus 12 is intended to be used on a substantially flat surface. In variations, the wheel clearance is adjustable, including possibly being dynamically adjustable in response to sensed terrain features.

In at least some embodiments, the system 10 is operable to take precise voltage differential measurements using an autonomous robot (apparatus 12) allowing for the calculation and capture of thousands of vector points. Such robot allows for the detection and locating of defects under minimal or no supervision, thereby advantageously reducing the need for expert operators. Suitable algorithms for robotic guidance allow the robot to traverse the test area efficiently while providing adequate coverage.

The apparatus 12 of the second embodiment need not include the handle 40. Additionally or alternatively, the second embodiment may include the handle 40 being removably attachable to the wheeled base 68, with FIGS. 3 and 4 showing the handle 40 removed from the wheeled base 68.

Figure 5:
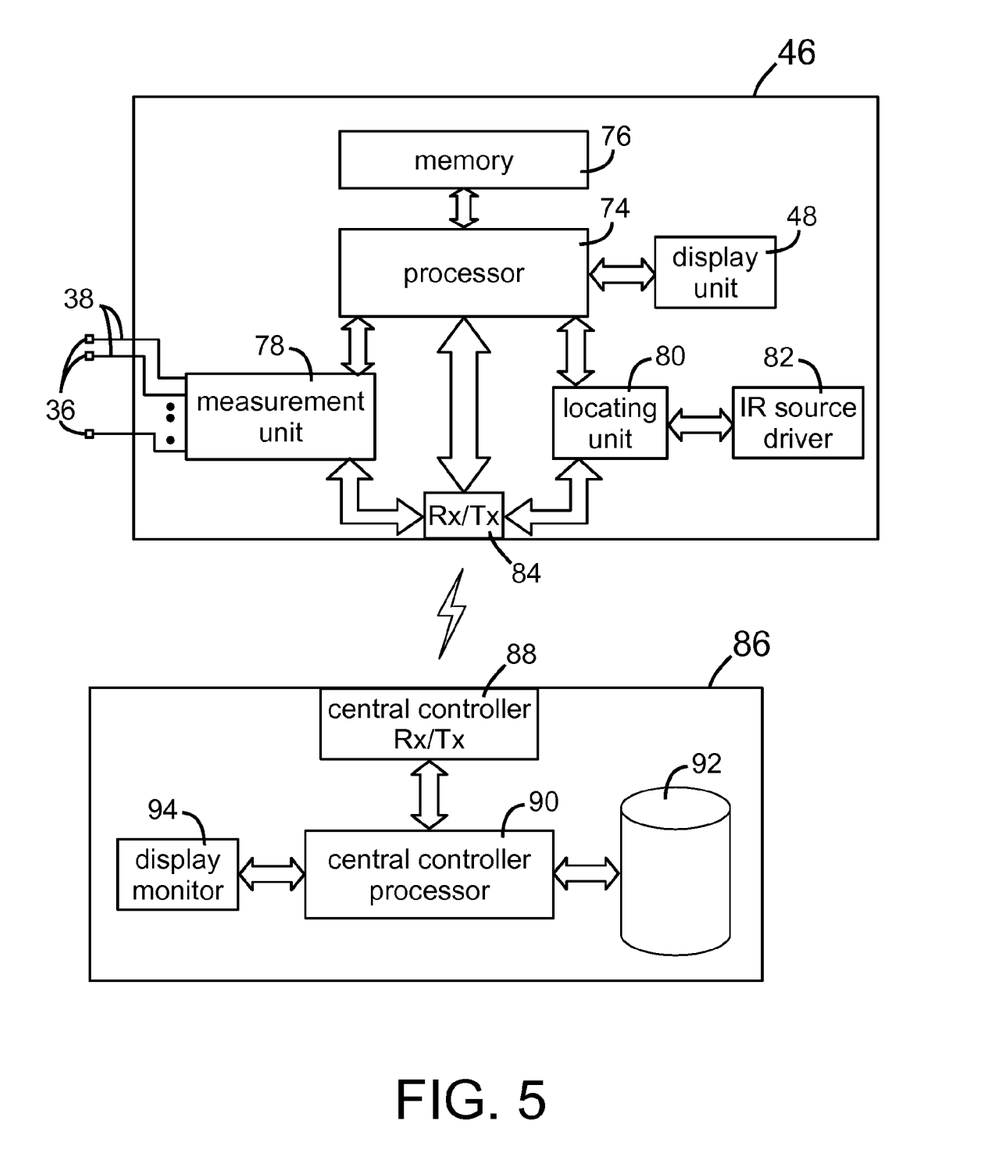
FIG. 5 is a block diagram of a system having a controller according to the first or second embodiment of the invention.

Referring to FIG. 5, the controller 46 in accordance with the first embodiment, the second embodiment, or both the first and the second embodiment includes a processing circuit, such as the processor 74, and a memory, such as the memory circuit 76.

The processor 74 is typically a processing circuit that includes one or more circuit units, such as a central processing unit (CPU), digital signal processor (DSP), embedded processor, etc., and any combination thereof operating independently or in parallel, including possibly operating redundantly. The processor 74 may be implemented by one or more integrated circuits (IC), including being implemented by a monolithic integrated circuit (MIC), an Application Specific Integrated Circuit (ASIC), a Field Programmable Gate Array (FPGA), etc. or any combination thereof. Additionally or alternatively, the processor 74 may be implemented as a programmable logic controller (PLC), for example. The processor 74 may include circuitry for storing memory, such as digital data, and may comprise the memory circuit 76 or be in wired communication with the memory circuit 76, for example.

The memory circuit 76 is operable to store digital representations of data or other information, including measurement data, and to store digital representations of program data or other information, including program code for directing operations of the processor 74.

Typically, the memory circuit 76 is all or part of a digital electronic integrated circuit or formed from a plurality of digital electronic integrated circuits. The memory circuit 76 may be implemented as Read-Only Memory (ROM), Programmable Read-Only Memory (PROM), Erasable Programmable Read-Only Memory (EPROM), Electrically Erasable Programmable Read-Only Memory (EEPROM), flash memory, one or more flash drives, universal serial bus (USB) connected memory units, magnetic storage, optical storage, magneto-optical storage, etc. or any combination thereof, for example. The memory circuit 76 may be operable to store digital representations as volatile memory, non-volatile memory, dynamic memory, etc. or any combination thereof.

The controller 46 of the first and/or second embodiments includes the measurement unit 78 connected to one or more probe terminations 36 and/or one or more guard terminations 60 (FIG. 2), which may be via the probe connections 38. The measurement unit 78 is operable in various embodiments to perform measurements in accordance with any suitable technique for detecting a defect or otherwise sensing an indication of a defect, including measuring electrical current flow within the water 24 (FIGS. 1 and 3). In exemplary embodiments, the measurement unit 78 includes a 24-bit or higher analog-to-digital converter (not shown) for wide range and precise voltage differential measurements.

The controller 46 is typically operable to control the operation of the measurement unit 78 such that one or more measurements of electrical current flow within the water 24 via one or more probe terminations 36 and/or guard terminations 60 are performed, which includes in some embodiments computing an average of multiple measurement results obtained using a given pair of probe terminations 36 and/or guard terminations 60 at a given location of the apparatus 12.

In embodiments where the probe terminations 36 of multiple probes 34 are each aligned along a different axis defining an axial direction, the controller 46 is operable to measure the magnitude of electrical current flow within the water 24 associated with each axial direction and compute a resultant measurement vector indicative of the magnitude, or average magnitude, and direction of electrical current flow within the water 24. The controller 46 is further operable in various embodiments to store resultant measurement vectors in the memory 76.

The processor 74 may also direct the display unit 48 to provide a display of such resultant measurement vectors.

In at least some embodiments, the processor 74 comprises the measurement unit 78 and/or is operable to perform all or part of the functionality of the measurement unit 78. In some embodiments, the measurement unit 78 is a Wireless Data Acquisition Device (WiDAQ™) unit manufactured by SMT Research Ltd.

In the exemplary embodiment shown in FIG. 5, the controller 46 includes a locating unit 80 forming part of the system 10 functionality for determining the location of the apparatus 12. The locating unit 80 may be or include a global positioning system receiver, for example. In embodiments implementing automated vision as described herein with reference to FIGS. 1 and 3, the locating unit 80 is preferably in communication with the infra-red source driver 82 for providing power to the markers 56 (FIGS. 1 and 3). In at least some embodiments, the processor 74 comprises the locating unit 80 and/or is operable to perform all or part of the functionality of the locating unit 80.

As indicated in FIG. 5, any one or more of the processor 74, the measurement unit 78 and the locating unit 80 may be in communication with a transceiver 84 for conducting external communications.

The system 10 in the exemplary embodiment shown in FIG. 5 includes a central controller 86 in communication with the controller 46. As shown by way of example in FIG. 5, the central controller 86 includes a central controller transceiver 88 for communicating with the controller 46; a central controller processor 90 for performing computations of the central controller 86 and/or the system 10 generally; a database 92 for storing data, including measurement data, of the system 10; and a display monitor 94 for displaying measurement results and other user information. The central controller transceiver 88, central controller processor 90, database 92 and display monitor 94 may be identical, similar, analogous or different from the transceiver 84, processor 74, memory 76 and display unit 48 as described herein, respectively.

In exemplary embodiments, the central controller 86 is operable to perform computations on measurement results to produce statistical or other aggregated data; store system 10 data; display system 10 data; generate reports, alerts, alarms or other system 10 output such as in response to measurement results and/or other system 10 data; receive user input; control operation of the apparatus 12; cause adjustments of parameters of the apparatus 12, such as measurement gain, or otherwise control the operation of the apparatus 10; cause adjustment of parameters of the electrical generator 26 or otherwise control the operation of the electrical generator 26; cause adjustments of parameters of the system 10 or its components such as in response to user input; determine the location of the apparatus 12; communicate by wired and/or wireless communications with system 10 components; communicate wirelessly with remote systems (not shown), such as by network communications; perform system 10 administrative functions; other similar or comparable functions or operations; or any combination thereof, for example.

By way of example, the central controller 86 may be any computing device such as a general purpose computer, microcomputer, minicomputer, mainframe computer, distributed network for computing, functionally equivalent discrete hardware components, etc., and any combination thereof for example.

While FIG. 5 shows exemplary two-way wireless communications between the controller 46 and the central controller 86, one-way communications may be used for transmitting measurement results, such as resultant measurement vectors, from the apparatus 12 to the central controller 86. In embodiments using the reference cable 62, wired communications may be effected between the apparatus 12 and the central controller 86 such that wireless communications between the apparatus 12 and the central controller 86 need not be implemented at all.

In various embodiments, various functions of the controller 46 may be additionally or alternatively performed by the central controller 86, and various functions of the central controller 86 may be additionally or alternatively performed by the controller 46. In some embodiments, the controller 46 comprises the central controller 86.

Figure 6:
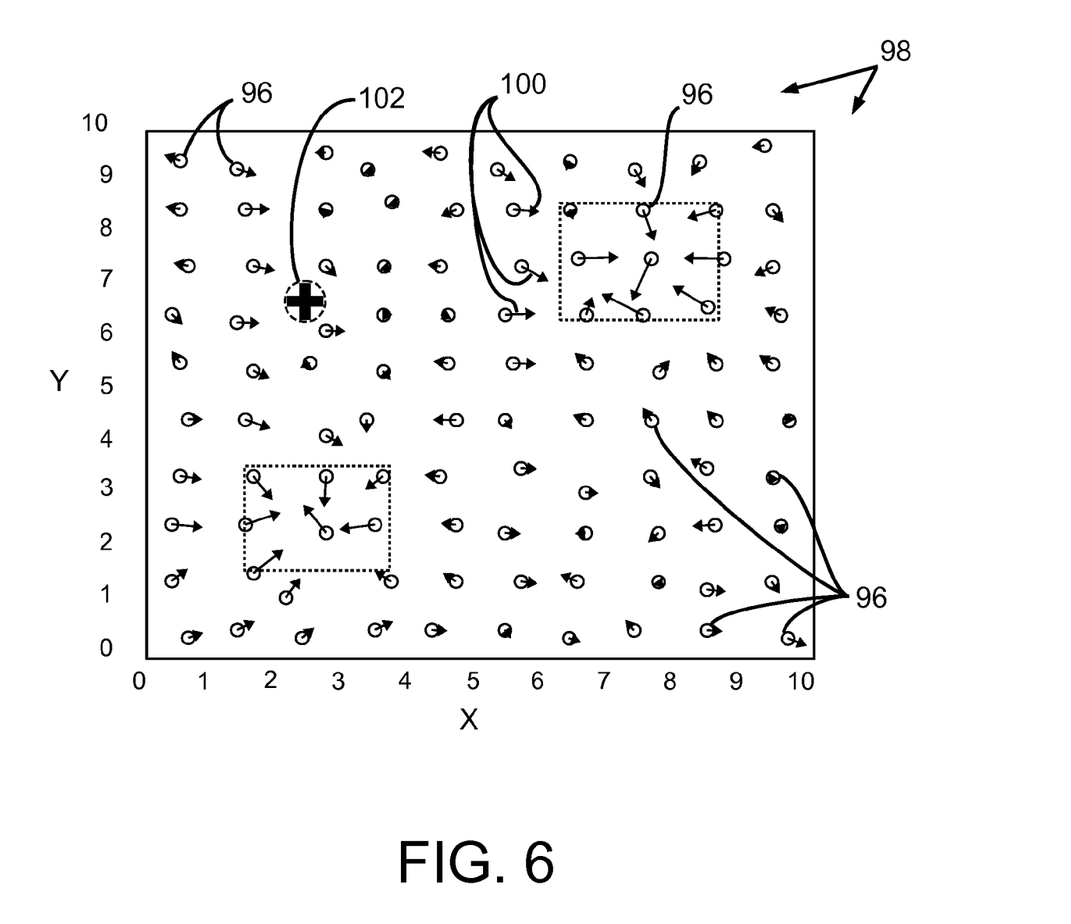
FIG. 6 is a graphical representation of a display produced by the system shown in FIG. 5, showing a plurality of resultant measurement vectors.

Referring to FIG. 6, the system 10 is preferably operable to produce a display of a plurality of resultant measurement vectors in association with location information. Such display may be produced on the display unit 48, on the display monitor 94, on a further remote display device (not shown), in a printed report, by a similar or related technique, or any combination thereof, for example.

FIG. 6 shows locations at which measurements producing a resultant measurement vector were performed by the apparatus 12. Each such location is represented graphically in FIG. 6 by a circle 96 on an X-Y plane 98 associated with the test area of the insulating layer 18, thereby forming an electric field vector map of the test area. The direction of electrical current flow within the water 24 at the location indicated by a given circle 96 is represented by the direction pointed by an arrow 100 associated with the given circle 96. The magnitude of the electrical current flow at the location indicated by the given circle 96 is represented by the length of the associated arrow 100. Generally, the direction pointed by the arrows 100 indicate the direction toward the closest leak 14 and the length of the arrow 100 indicates the distance to the closest leak 14.

The system 10 as shown in FIG. 6 is operable to determine from a number of resultant measurement vectors the location of any leaks 14 that are present, and represent such leak 14 locations graphically. In FIG. 6, two leak 14 locations are represented by rectangles drawn in dotted line. Further displays may be produced, including contour maps (not shown) showing lines of constant vector magnitude within the X-Y plane 98; 3-dimensional mesh drawings (not shown) indicating vector magnitudes in a third dimension perpendicular to the X-Y plane 98; and displays registered with images of the test area for ease of identifying leak 14 locations; other similar or related displays; and any combination thereof, for example.

As shown in FIG. 6, the system 10 is operable to detect, locate and map multiple defects or other penetrations in the building structure 16, advantageously without requiring each located leak 14 to be excluded from the test area in order to detect and locate further leaks 14.

Any number of visual features such as resultant measurement vectors and/or associated locations may be displayed, including displaying all or a portion of one or more sets of resultant measurement vectors produced by one or more scans by the apparatus 12 of the test area or sub-area thereof. Multiple scans within a test area may occur in which the distance between measurement locations is altered, for example, in response to measurement data including collecting more measurements located more closely to each other in the vicinity of a previously located leak 14. In at least some embodiments, the system 10 is operable to display visual features at specifiable zoom settings.

Additionally or alternatively, the system 10 is operable in at least some embodiments to successively display any number of visual features, including displaying resultant measurement vectors and/or associated locations in the order in which measurements were made at any specifiable playback speed, including slow motion and fast forward speeds; in an order opposite to the order in which measurements were made (e.g. reverse playback) at any specifiable speed; or any combination thereof. The measurements from multiple measurement sessions may be displayed simultaneously to form a composite display, may be displayed successively to demonstrate changes in the leakage status of a given test area over time, or any combination thereof.

Still referring to FIG. 6, the present location 102 of the apparatus 12 may be displayed, such as in conjunction with a vector map and/or image of the test area or sub-area thereof. Although not necessarily shown to scale in FIG. 6, the present location 102 of the apparatus 12 may be displayed so as to indicate the size of the apparatus 12 relative to distances displayed on the vector map and/or image of the test area. Displaying the present location 102 advantageously facilitates locating the apparatus 12, locating the location at which a given measurement was made, returning to the location of a previously located leak 14, or any combination thereof. In at least some embodiments, the system 10 is operable to dynamically update the indication of the present location 102 on a display, thereby advantageously guiding a user from a starting location to a desired new location, such as that of a previously located leak 14. Additionally or alternatively, the system 10 is operable in some embodiments to display an indication of a path (not shown), such as a path defined between two locations within a test area, or sub-area thereof, including a path between the present location 102 of the apparatus 12 and a closest identified leak 14 for example.

The apparatus 12 in at least some embodiments is operable to successively change its location so as to traverse a path, which may for example be a path determined by system 10 in response to measurement data, determined from user input, determined in response to parameters of the test area, or any combination thereof.

Additionally or alternatively, the autonomous apparatus 12 in at least some embodiments is operable to autonomously move from its present location 102 to a desired location such as the location of a previously located leak 14, a point of origin defined within the test area, a starting location for commencing and/or resuming a scan, a location for a subsequent measurement within a given scan, or successively any combination thereof for example. Autonomously moving to the location of a previously located leak 14 advantageously permits the apparatus 12 to demonstrate to a human user the location of one or more leaks 14 after a scan has been completed for example. Upon arriving at the desired location, the autonomous apparatus 12 in at least some embodiments is operable to take certain action such as producing a light, sound, identifying movement (e.g. spinning, back-and-forth motion, etc.), or any combination thereof, to indicate it is presently located at the desired location.

While embodiments of the invention have been described and illustrated, such embodiments should be considered illustrative of the invention only. The invention may include variants not described or illustrated herein in detail. For example, certain aspects of the system 10 may be permanently installed and maintained for periodic automated scanning of the building structure 14 test area; the autonomous apparatus 12 may be programmed to take certain action upon locating a leak 14, such as producing a visible marking of the location on the insulating layer 16; the system 10 may be operable to determine and graphically represent terrain dimensions associated with the insulating layer 18; and other variants. Thus, the embodiments described and illustrated herein should not be considered to limit the invention as construed in accordance with the accompanying claims.

What is claimed is:
1. An apparatus for detecting a defect in a building structure, the apparatus comprising:
(a) a moveable base comprising a pair of spaced-apart terminals defining a probe attached to and projecting from said moveable base, said terminals being dimensioned for immersing into a fluid situated adjacent a first side of an electrically insulating member of the building structure, said electrically insulating member being supported at a second side thereof by an electrically conductive support of the building structure, the apparatus being operable to produce a measurement of electrical current flow within said fluid between said terminals when said terminals are contacting said fluid and a potential difference is being generated between said electrically conductive support and said fluid, the apparatus being operable to determine, at a first location of the apparatus in response to said measurement produced at said first location only, an indication of the direction from said first location toward the defect; and
(b) a transmitter operable to wirelessly transmit said indication from the apparatus to a central controller.
2. The apparatus of claim 1 further comprising a locator operable to determine said first location, and wherein said transmitter is operable to wirelessly transmit to said central controller said first location in association with said indication.
3. The apparatus of claim 2 wherein said locator comprises at least one of an automated vision system, a global positioning system, a local beacon positioning system, an odometer, an optical sensor and an accelerometer.
4. The apparatus of claim 1 comprising a plurality of said probes aligned in different directions from each other.
5. The apparatus of claim 4 comprising a processor operable to determine, from a plurality of said measurements associated with said plurality of probes, respectively, a resultant measurement vector indicating said direction from said first location toward the defect and the distance of the defect from said first location.
6. The apparatus of claim 5 comprising a display having a display screen, the apparatus being operable to display said resultant measurement vector on said display screen.
7. The apparatus of claim 1 comprising a substantially circular guard electrically connectable to said electrically conductive support, said guard terminating in one or more guard terminals dimensioned for immersing into said fluid.
8. The apparatus of claim 1 further comprising a handle attachable to said base.
9. A system for detecting a defect in a building structure, the system comprising:
(a) a detection unit comprising a moveable base, said moveable base comprising a pair of spaced-apart terminals defining a probe attached to and projecting from said moveable base, said terminals being dimensioned for immersing into a fluid situated adjacent a first side of an electrically insulating member of the building structure, said electrically insulating member being supported at a second side thereof by an electrically conductive support of the building structure, said detection unit being operable to produce a measurement of electrical current flow within said fluid between said terminals when said terminals are contacting said fluid and a potential difference is being generated between said electrically conductive support and said fluid, said detection unit being operable to determine, at a first location of said detection unit in response to said measurement produced at said first location only, an indication of the direction from said first location toward the defect;
(b) a locator operable to determine said first location; and
(c) a memory for storing said indication and said first location in association with each other.
10. The system of claim 9 wherein said detection unit comprises a device selected from the group consisting of: a negative pressure containment device, a smoke detection device, a humidity detection device and an electrical field detection device.
11. The system of claim 9 wherein the system is operable to determine the distance of the defect from said first location.
12. The system of claim 9 wherein said detection unit comprises a plurality of said probes aligned in different directions from each other.
13. The system of claim 12 wherein at least one of said detection unit and a central controller in communication with said detection unit is operable to determine, from a plurality of said measurements associated with said plurality of probes, respectively, a resultant measurement vector indicating said direction from said first location toward the defect and the distance of the defect from said first location.
14. The system of claim 13 wherein at least one of said detection unit and said central controller is operable to display said resultant measurement vector on a pixel display.
15. The system of claim 13 comprising a building guard adjacent said electrically insulating member at said first side, and an electrical source connectable between said building guard and said electrically conductive support, said electrical source being operable to generate said potential difference.

16. The system of claim 9 further operable to adjust a measurement gain of said detection unit and adjust said potential difference.

17. The system of claim 9 wherein said locator comprises at least one of an automated vision system, a global positioning system, a local beacon positioning system, an odometer, an optical sensor and an accelerometer.

18. The system of claim 9 wherein said detection unit comprises a substantially circular guard electrically connectable to said electrically conductive support.

19. A method of detecting a defect in a building structure, the method comprising:
(a) generating an electrical potential difference between an electrically conductive support of the building structure and a fluid situated adjacent a first side of an electrically insulating member of the building structure, said electrically insulating member being supported at a second side thereof by said electrically conductive support;
(b) producing, by a detection unit at a first location of said detection unit, a measurement of electrical current flow within said fluid between a pair of spaced-apart terminals defining a probe attached to and projecting from a moveable base of said detection unit when said terminals are contacting said fluid;
(c) determining, by said detection unit at said first location in response to said measurement produced at said first location only, an indication of the direction from said first location toward the defect;
(d) determining said first location; and
(e) storing in a memory said indication and said first location in association with each other.

20. The method of claim 19 further comprising determining the distance of the defect from said first location.

21. The method of claim 19 wherein producing, by a detection unit at a first location of said detection unit, a measurement of electrical current flow within said fluid between a pair of spaced-apart terminals defining a probe attached to and projecting from a moveable base of said detection unit when said terminals are contacting said fluid comprises producing a plurality of said measurements associated with a plurality of said probes aligned in different directions from each other, respectively.

22. The method of claim 21 wherein determining, by said detection unit at said first location in response to said measurement produced at said first location only, an indication of the direction from said first location toward the defect comprises determining from said plurality of measurements a resultant measurement vector indicating said direction from said first location toward the defect and the distance of the defect from said first location.

23. The method of claim 19 further comprising transmitting said indication to a central controller by wireless communications.

24. The method of claim 22 further comprising displaying said resultant measurement vector on a pixel display.

25. The method of claim 19 further comprising repeating steps (b), (c), (d) and (e) of claim 19 at a second location.

26. The method of claim 25 wherein said second location is closer to the defect than said first location.

* * * * *